(12) United States Patent
Pompella et al.

(10) Patent No.: US 8,148,099 B2
(45) Date of Patent: Apr. 3, 2012

(54) PROCESS FOR DETERMINING S-NITROSOTHIOLS IN BIOLOGICAL FLUIDS

(75) Inventors: Alfonso Pompella, Pisa (IT); Aldo Paolicchi, San Giuliano Terme (IT); Emilia Bramanti, Pietrasanta (IT); Renata Barsacchi, Lucca (IT); Maria Franzini, Calci (IT); Cecilia Vecoli, Pietrasanta (IT)

(73) Assignee: Universita' Di Pisa, Pisa (IT)

( * ) Notice: Subject to any disclaimer, the term of this patent is extended or adjusted under 35 U.S.C. 154(b) by 356 days.

(21) Appl. No.: 12/309,623

(22) PCT Filed: Jul. 23, 2007

(86) PCT No.: PCT/IB2007/002090
§ 371 (c)(1),
(2), (4) Date: Jun. 17, 2009

(87) PCT Pub. No.: WO2008/012642
PCT Pub. Date: Jan. 31, 2008

(65) Prior Publication Data
US 2009/0275012 A1 Nov. 5, 2009

(30) Foreign Application Priority Data

Jul. 21, 2006 (IT) .................. PI2006A0093

(51) Int. Cl.
*C12Q 1/37* (2006.01)
(52) U.S. Cl. ........................................... 435/24
(58) Field of Classification Search ............... 435/24
See application file for complete search history.

(56) References Cited

U.S. PATENT DOCUMENTS

2010/0227351 A1* 9/2010 Paolicchi et al. ............... 435/15

OTHER PUBLICATIONS

Bramanti E. et al. Exogenous vs. Endogenous Gamma Glutamyltransferase Activity. Archives of Biochemistry and Biophysics 487(2)146-152, Jul. 15, 2009.*

* cited by examiner

*Primary Examiner* — Ralph Gitomer
(74) *Attorney, Agent, or Firm* — Abelman, Frayne, Schwab

(57) ABSTRACT

A process for determining S-nitrosothiols, in particular S-nitrosoglutathione, in biological fluids that is easy, selective, cheap with respect to the prior art, which requires the use of equipment commonly available in laboratories, at low cost, which can be used by not qualified operators. The process is based on the hydrolysis of S-nitrosoglutathione (GSNO) by an enzyme, in particular γ-glutamyltranspeptidase (GGT). This enzyme hydrolizes the residual γ-glutamyl of GSNO for giving glutamate (GIu) and S-nitroso-cysteinylglycine (GIy-CySNO). In the presence of ions of transition metals GGT speeds up the release of NO since the intermediate that is formed, the GIyCySNO, is much more sensitive to a metal-dependent decomposition. Advantageously, the amount of nitric oxide present in the sample is measured through a reaction thereof with 4,5 diaminof luorescein (DAF-2), said reaction creating a fluorescent compound in an amount proportional to the S-nitrosothiol amount present in the sample. Alternatively, the amount of released NO can be measured by a chemiluminescence analyser, commercially available. In the presence of biological fluids having complex matrix, the introduction of the enzyme is done after separation of the S-nitrosothiol from the other components of the fluid.

14 Claims, 7 Drawing Sheets

PROCESS FOR DETERMINING S-NITROSOTHIOLS IN BIOLOGICAL FLUIDS

CROSS-REFERENCE TO RELATED APPLICATIONS

This application is a National Phase of PCT/IB2007/002090, filed Jun. 23, 2007, which claims the priority of IT PI 2006 A 000093, filed Jun. 21, 2006, both of which are incorporated herein by reference.

FIELD OF THE INVENTION

The present invention relates to a process for determining the content of S-nitrosothiols, in particular S-nitrosoglutathione, in biological fluids.

BACKGROUND OF THE INVENTION

Nitric oxide (NO), released at endothelial level, plays an essential role in the regulation of vessel tone and is considered an essential molecule in the regulation of cardiovascular system. It has been recently hypothesized that NO, besides having a paracrine effect, is also capable of acting under an endocrine mechanism, inducing a vessel-active action in zones that are remote from the biosynthesis/delivering site.

In particular, it is supposed that high doses of NO, delivered via inhalation, can be beneficial not only at pulmonary level, but also at systemic level, and that an intravenous infusion of a NO solution can cause vasodilation.

Owing to the brief half life of NO in the hematic area (about 2 ms), the endocrine effect of NO is supposed to be mediated by steady and bioactive carrying mechanisms, capable of guiding NO from biosynthesis delivery sites of to ischemic/hipoxic zones. Presently different forms of deposition and transport of NO at hematic level have been observe: S-nitrosocysteine, S-nitrosoglutathione (defined as low molecular weight nitrosothiols, LMW-RSNOs), as well as S-nitrosoalbumin and S-nitrosohemoglobin (defined as high molecular weigth nitrosothiols, HMW-RSNOs), for which the radical R represents an aminoacid, a polypeptide and a proteine respectively. Such compounds are capable of releasing NO.

The presence at hematic level of these forms of deposition of NO, whose levels increase in a significant way after inhalation of NO or by supplying NO-donor drugs, has been confirmed by many researches in different animal models and in humans (as described by Cannon et al. above cited). However their actual contribution in conservative NO metabolisms have still to be defined, as well as their task and their relevance in physiological and pathological conditions.

It has also been supposed that some NO molecules are displaced by nitrosylhemoglobin to the residual of cysteine 93 of hemoglobin beta chain, forming S-nitroso-hemoglobin (SNO-Hb) that could act as vasodilator (Gladwin M T, Schechter AN Circ Res. 2004,94,851).

Some authors (Deem S Free Radic Biol Med. 2004,36, 698-706) hypothesize that, at peripheral level, when Hb releases oxygen to the tissues, SNO-Hb is capable of conveying and releasing NO in bioactive form.

In addition to the involvement of NO and of its derivatives in the cardiovascular system, many authors have described other effects of nitric oxide, among which the following can be cited: nitric oxide and S-nitrosothiols have antimicrobial effects (De Groote M A Fang F C Clin Infect Dis. 1995, Suppl. 2, S162-5), inhibit platelet aggregation (Hirayama A, Noronha-Dutra A A, Gordge M P, Neild GH, Hothersall J S Nitric Oxide, 1999, 3, 95-104), are bronchodilators (Bannenberg G, Xue J, Engman L, Cotgreave I, Moldeus P, Ryrfeldt A J Drugl Exp Ther, 1995, 272, 1238-45), inhibit the intestinal motility (Slivka A, Chuttani R, Carr-Locke DL, Kobzik L, Bredt D S, Loscalzo J, Stamler J S. J Clin Invest. 1994, 94, 1792-8) and are involved in different regulation processes of the central nervous system, such as nhibition of lipidic peroxidation and of oxidative damage (Rauhala P, Lin A M, Chiueh C C. FASEB J. 1998, 12, 165-73), as well as of peripheral nervous system and of the immunologic system.

Therefore, endogenous and/or esogenous compounds capable of releasing NO, known as NO-donor molecules, in the body are of high scientific interest.

In particular, S-nitrosoglutathione (GSNO), present in plasma and in lung and brain extracellular fluids, has different biological effects. GSNO is capable of, for example, relaxing the smooth muscle of the respiratory system, increasing the ciliary motility, to inhibit transfer of amiloride-sensitive sodium in epithelium aerial ducts.

A specific use of S-nitrosothiols, and, in particular, of GSNO, is described in WO95/07691. It teaches the therapeutic or prophylactic use of GSNO, for treatment of thrombosis of damaged vascular areas.

In EP 412699, instead, the use is described of S-nitrosothiols as therapeutic agent for cardiovascular diseases, in particular against hypertension, and for treatment of angina pectoris.

The steadiness of S-nitrosothiols depends on different factors, in particular the characteristics of radical R, heat, light, the presence of ions of transition metals, the presence of other thiols, etc. Therefore, for fully exploiting the therapeutic and diagnostic potentiality it is necessary to study some biochemical, physiological and pharmacological aspects still not much known.

To this end it is relevant the ability to determine the amount of S-nitrosothiols in biological fluids (blood, plasma, saliva, urine, pulmonary fluid, liquor, amniotic fluid, etc.) through simple, rapide, precise and accurate techniques.

The methods for determining S-nitrosothiols (RSNO) in biological fluids can be classified as:

(i) Direct methods for RSNOs.

a) UV Spectrophotometry at 334 nm; owing to the low molar absorption coefficient ($\epsilon=977$ M-1 cm-1) of the S-nitroso unit, the detection by means of UV Spectrophotometry after chromatographic separation or electrophoresis (Capillary Zone Electrophoresis, CZE) limits its detection at micromolar level).

b) Electrochemical detectors (detection limit=1 μM)

(ii) Indirect methods, based on the decomposition of RSNOs according to the reactions:

RSNO→RSH/RSSR+NO

NO→nitrites/nitrates and on the detection of their metabolites:

a) NO;

b) nitrites;

c) reduced thiol(RSH)).

The decomposition of the S-nitrosocysteinyl group is presently carried out through photolysis or chemical reduction.

NO is revealed normally by means of chemiluminescence or electrochemical detector of Clark type or of planar amperometric type (detection limit=1 μM) or by means of electron spin resonance spectroscopy (EPR).

Chemiluminescence is based on the reaction of NO radical with ozone according to the reaction: NO•+O$_3$→NO$_2$+O$_2$γ
NO•+O$_3$+hν.

The EPR involves the entrapment of NO• by a complex with an eme-proteine that form a nitrosyl-eme-proteine. Both chemiluminescence and EPR are very sensitive techniques, but require dedicated measuring systems.

Nitrites can be revealed by means of various techniques like Griess reaction, fluorimetry and electrochemical detection coupled or not to liquid chromatography or to gas chromatography with mass spectrometry detector.

Chromatographic techniques and, in particular, high performance liquid chromatography (HPLC), allow separating two or more compounds present in a solvent exploiting the affinity balance between a "steady phase" located in a chromatographic column and a "mobile phase" that flows through the column same. The principle at the basis of this technique is that a substance more affine to the steady phase with respect to the mobile phase takes a longer time to cover the chromatographic column with respect to a substance with low affinity to the steady phase and high affinity for mobile phase. The sample to analyse is injected at the beginning of the chromatographic column where it is "pushed" through the steady phase by the mobile phase under high pressures. To obtain a effective separation it is necessary that the size of the filling particles is very low, and for this reason is necessary applying a high pressure if has to be maintained a reasonable flow rate of the eluent and then a suitable time of analysis. At the end of the column a detector is mounted (fluorimetric or spectrophotometric or eletrochemical detector), and a computer for quantifying and/or checking the injected substances.

However, the HPLC apparatus have very high costs and each single test requires very long time.

Some attempts have been made for determining S-nitrosothiols, like in WO 2006007403, where it is detected and measured the S-nitrosothiolic bond in cells and molecules containing the eme group.

Instead, in WO9710493 and U.S. Pat. No. 5,891,735 a method is described for measuring nitrosyl Fe(II)-hemoglobin, whereas WO9820336 relates to a method for detection of nitric oxide (NO) by means of EPR spectroscopy in fluids through the reactivity of NO with N-methyl-D-glucamine dithiocarbamate (MGD), a low molecular weight chelating compound, containing sulphide, complexed with iron ions [(MGD)2-Fe] Finally, in WO0216934 a test for S-nitrosothiols is described by means of EPR.

From the above it is apparent that the measurement of metabolytes of S-nitrosothiols (NO or nitrites) in biological fluids is difficult, and requires long and complex procedures of treatment of the samples, as well as equipment specialized. It is also known that the choice of the method for preparing the sample and the systems used to break the S-NO bond (photolysis, HgCl2, HgCl2/V(III), KI/I2, Cys/KI/Cu(I), Cu(I)/Cys, Cu(I)/KI/I2, CO/Cu(I)/Cys, DTT) represent a critical point for the purpose of obtaining reliable, precise and accurate analytical data.

Finally, the methods described above are aspecific, i.e. give a measurement of total RSNO present in the sample, but a differentiation (specification) of the only S-nitrosothiols can be carried out only through the use of chromatographic techniques.

It is also known that a higher difficulty associated with computing RSNO in biological fluids and, in particular, in plasma, is the physiological presence in such matrix of anti-oxidant and anti-free radical systems (uric acid, ascorbic acid, vitamines and, in particular, B12 vitamine). It has been hypothesized that whichever the mechanism is used to break the S—NO bond, once freed the NO radical, in the presence of such anti-oxidant and anti-free radical systems, the NO radical is quickly decomposed and not more revealable by fluorescent, or chemiluminescent probes, commonly used for detection of NO.

Owing to these difficulties, the different analytic approaches used, for example for determining RSNO in plasma, have given values that span over three orders of magnitude, from nanomolar concentration levels to micromolar concentration levels.

SUMMARY OF THE INVENTION

It is therefore an object of the present invention to provide a process for determining S-nitrosothiols, in particular S-nitrosoglutathione, in biological fluids that is easy and cheap with respect to the prior art.

It is another feature of the present invention to provide a process for determining S-nitrosothiols, in particular S-nitrosoglutathione, in biological fluids that requires equipment commonly available in laboratories, of low cost and large use, in order to be operated also by unqualified assistants.

It is also an object of the present invention to provide a process for determining S-nitrosothiols, in particular S-nitrosoglutathione, in biological fluids that is highly selective, where selectivity is given by an enzymatic reaction capable of releasing a nitrosylated peptide according to reactions (1), or (2) and/or (3):

(1) R'—CySNO—R"→R'—CySNO+R"

(2) R'—CySNO—R"+light→R'—Cys—R"+NO (3) R'—CySNO—R"+metals and/or chemical reducing agents→metal oxidized or complexed products of R'—Cys—R"+NO.

where CySNO is a residual of nitrosylated cysteine and R' and R" are aminoacids or peptides or polypeptides.

It is a particular feature of the present invention to provide a process for determining S-nitrosothiols, in particular S-nitrosoglutathione, in biological fluids having not complex matrix, such as in particular organ perfusates, washing fluids of organs, fluids for in-vitro analysis, buffer solutions.

It is another particular feature of the present invention to provide a process for determining S-nitrosothiols, in particular S-nitrosoglutathione, in biological fluids having complex matrix, such as, in particular, in blood plasma, blood, urine, cell cultures, tissue extracts of organs, pulmonary fluids, where said matrix have anti-oxidant and anti-free radical systems (uric acid, ascorbic acid, vitamines and in particular B12 vitamine).

These and other features are accomplished with one exemplary process, according to the invention, for determining the content of S-nitrosothiols in biological fluids comprising the following steps:
  arranging a biological fluid sample in a container,
  introducing in the container a measured amount of an enzyme adapted to react in a selective way with a S-nitrosothiol present in the sample, causing a catalytic decomposition thereof into a nitrosylated intermediate product with subsequent release of nitric oxide (NO), or a derivative thereof, such as dinitrogen trioxide $N_2O_3$, nitrite ion $NO^{2-}$,
  computing the amount of nitric oxide, or of its derivatives, said amount being proportional to the S-nitrosothiol amount present in the sample.

In particular, if the determination is sought of the amount of S-nitrosoglutathione in a sample of a biological fluid, the enzyme may be γ-glutamyltranspeptidase (GGT).

Advantageously, the amount of nitric oxide present in the sample is measured through a reaction thereof with a fluorescent molecule, said reaction creating a fluorescent compound in an amount proportional to the S-nitrosothiol amount present in the sample.

Preferably, said fluorescent compound is 4,5 diaminofluorescein (DAF-2). More in detail, 4,5 diaminofluorescein does not react directly with NO but with an active intermediate thereof that is formed in the presence of $O_2$ giving rise to a highly fluorescent green tone compound, i.e. triazole fluorescein. The quantic efficiency of fluorescence of this triazolic type is 180 times larger than that of DAF.

Alternatively, the amount of released NO can be measured by a commercially available chemiluminescence analyser.

Normally, the amount of released NO can be determined with a detector selected from the group comprised of:

UV detector;
electrochemical detector;
fluorescence detector.

In particular, the introduction in the container of said measured amount of said enzyme can be done downstream of a flow-injection apparatus (FIA). The flow-injection technique has the advantage with respect to batch techniques of allowing an automatic, sequential and quick analysis of the samples (4 min/analysis) when interfering such molecules such as anti-oxidant, anti-free radicals molecules, etc., are not present.

Advantageously, the introduction in the container of said measured amount of said enzyme is done after separating said S-nitrosothiol from the other components contained in said organic fluid.

In particular, the separation of said S-nitrosothiol from said other components of the organic fluid can be made by a separative technique, in particular in liquid phase, selected from the group comprised of:

liquid chromatography, in particular, high pressure liquid chromatography (HPLC);
capillary electrophoresis;
precipitation in liquid phase.

In biological fluids having, complex matrix, the separation of the S-nitrosothiol from the other components of the biological fluid allows, in particular, to analyse also complex substances comprising interfering molecules such as antioxidant, anti-free radicals molecules, etc. that would negatively affect the analysis same.

In particular, in case of plasma the presence of the interfering molecules, i.e. of uric acid, of ascorbic acid and of dehydroascorbic acid does not allow determining with precision the NO radicals and then the S-nitrosothiol amount. Liquid chromatography, instead, allows to exceed this drawback separating GSNO from the "noise" plasmatic components, or interfering molecules, exploiting the different chemical properties of the various substances versus polarity, hydrophobicity and electric charge.

In particular, in liquid chromatography, the different plasmatic components are held in a column in a different way and have, therefore, different retention time (tR).

Advantageously, the enzyme used for the decomposition reaction, for example γ-glutamyltranspeptidase (GGT), is mixed in continuous flow with an eluate coming from a chromatographic column in which the separation is carried out of the biological fluid into its components. Therefore, the enzyme contacts separately the components of the eluate reacting only with the S-nitrosothiol causing the above described catalytic decomposition.

Advantageously, the enzyme is mixed in continuous flow with the eluate after mixing it with a measured amount of a fluorescent molecule, for example 4,5 diaminofluorescein (DAF-2), obtaining a derivatizing mixture. In particular, the fluorescent molecules of the derivatizing mixture reacts with the intermediate nitrosylated product formed from the reaction of the enzyme with the S-nitrosothiol giving rise to the fluorescent compound in an amount proportional to the amount of said S-nitrosothiol present in the biological fluid sample.

Since the enzymatic reaction is specific and selective for GSNO, the fluorescence signal derived from the reaction of NO freed in solution with DAF is observed only at the exit from GSNO column.

Advantageously, said eluate and said derivatizing mixture mixed to each other are fed to a thermostatic bath, said thermostatic bath being adapted to increase the speed of the enzymatic decomposition reaction.

Advantageously, the derivatizing mixture comprises:
γ-glutamyltranspeptidase (GGT);
Copper sulphate;
Diaminofluorescein (DAF).

Preferably, the catalytic decomposition is made using as catalyst a transition metal, selected from the group comprised of: iron (Fe), copper (Cu), molybdenum (Mo), vanadium (V), platinum (Pt), ruthenium (Ru), iridium (Ir), rhodium (Ro), nickel (Ni), palladium (Pd), zinc (Zn).

BRIEF DESCRIPTION OF THE DRAWINGS

The invention will be made clearer with the following description of some examples, not limitative with respect to the invention, with reference to the attached drawings wherein.

Principles of the method according to the invention S-nitrosoglutathione (GSNO) is a substrate of γ-glutamyl-transpeptidase (GGT). This enzyme hydrolyzes the residual γ-glutamyl of GSNO for giving glutamate (Glu) and S-nitroso-cysteinylglycine (GlyCySNO). The Km constant (Michaelis-Menten kinetic constant) of GGT for GSNO is 28 µM. In the presence of ions of the transition metals, GGT speeds up the release of NO since the intermediate that is formed, the GlyCySNO, is further responsive to the metal-depending decomposition.

Figure 1:
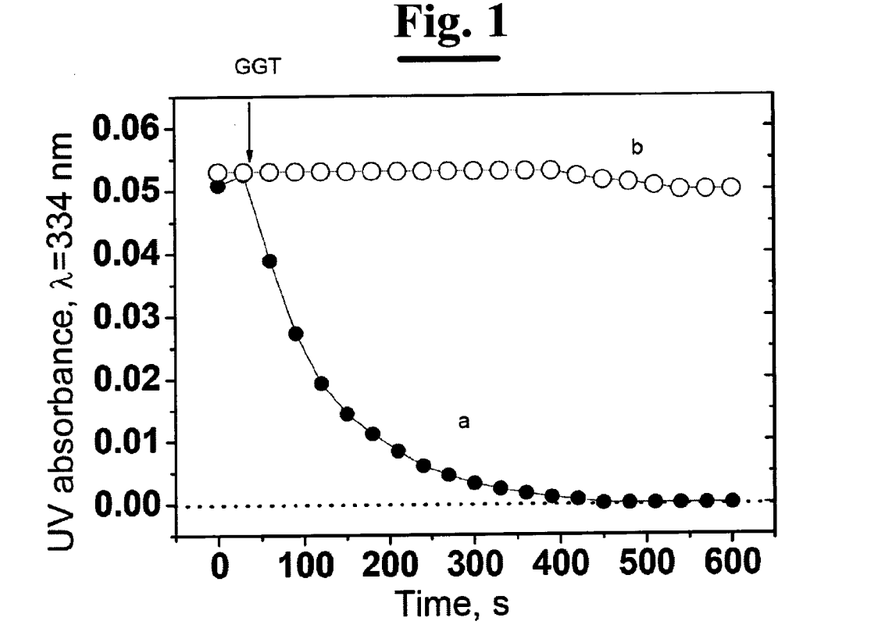
FIG. 1 shows a diagram of the decomposition kinetics of S-nitrosoglutathione (GSNO)

GSNO has a absorption band at 334 nm. FIG. 1 shows the effect of GGT on the steadiness of GSNO in buffer solution (phosphate buffer 0.1 M, pH 8.0) containing GlyGly 4.5 mM, Cu($SO_4$) 100 uM, GSNO 50 uM. In FIG. 1 in particular, the decomposition kinetics is shown of 50 uM GSNO with GGT 525 mU/mL added at the time t=0. In ordinates the absorbance at 334 nm is shown. Reaction mixture: phosphate buffer 0.1 M, pH 8.0, GlyGly 4.5 mM, Cu(SO4) 100 uM.

At the addition of GGT 525 mU/mL the decrease is observed of the absorbance at 334 nm that indicates the decomposition of GSNO (curve a of FIG. 1). GSNO is quantitatively decomposed, in the adopted operative conditions, in 450 sec. It is noticeable that by adding only 50 uM of $CuSO_4$ no decrease is observed of the absorbance at 334 nm since the intermediate GlyCySNO is steady and has an absorption at 334 nm similar to that of GSNO (curve b of FIG. 1).

NO freed in the solution can be advantageously revealed by a reaction with 4,5-diaminofluorescein (DAF) and a detection step by means of a spectrofluorimeter ($\lambda_{ex}$=480 nm, $\lambda_{em}$=515 nm) or by means of a automatic reader with ELISA plates ($\lambda_{ex}$=485±15 nm, $\lambda_{em}$=535±25 nm), or by means of a chemi-luminescence analyser. All these systems are available on the market.

Figure 2:
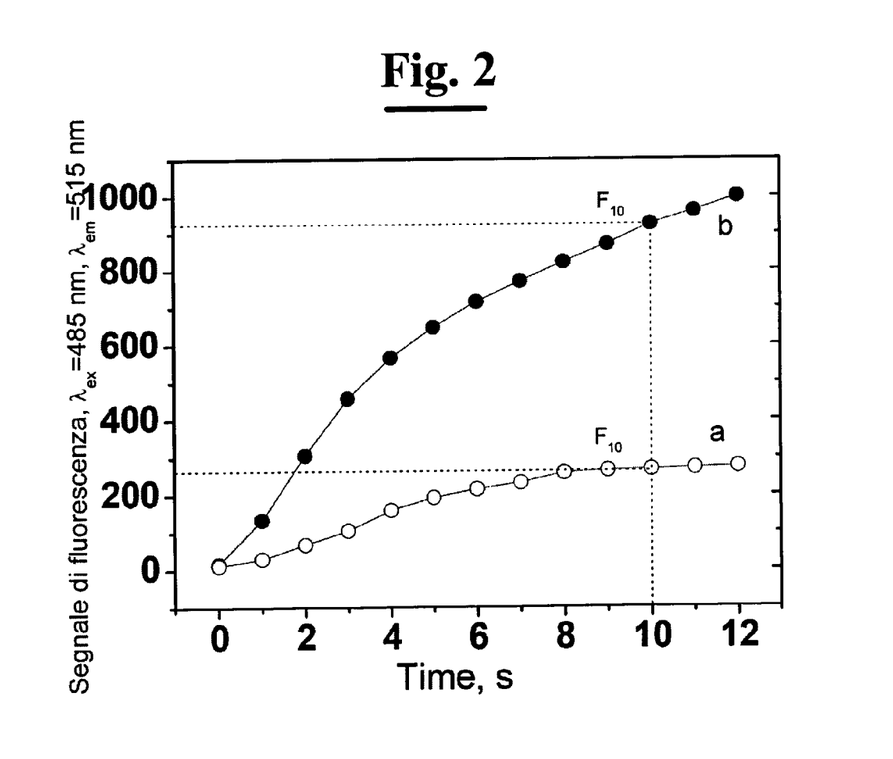
FIG. 2 shows the kinetic of formation of diaminofluorescein (DAF-2T) in the presence of GSNO.

FIG. 2 shows the kinetic of formation of DAF-2T in the presence of GSNO 100 nM (curve a) and 1000 nM (curve b). The reaction mixture consists of: PBS 0,1 M pH 8, $CuSO_4$ 100 uM, in 100 uM, GlyGly 4.5 mM, DAF 0,1 uM, GGT 525 mU/ml. GSNO is added at the time t=0. Kinetic of formation of DAF-2T in the presence of GSNO 100 and 1000 nM in phosphate buffer 0.1 M, pH 8.0.

Figure 3:
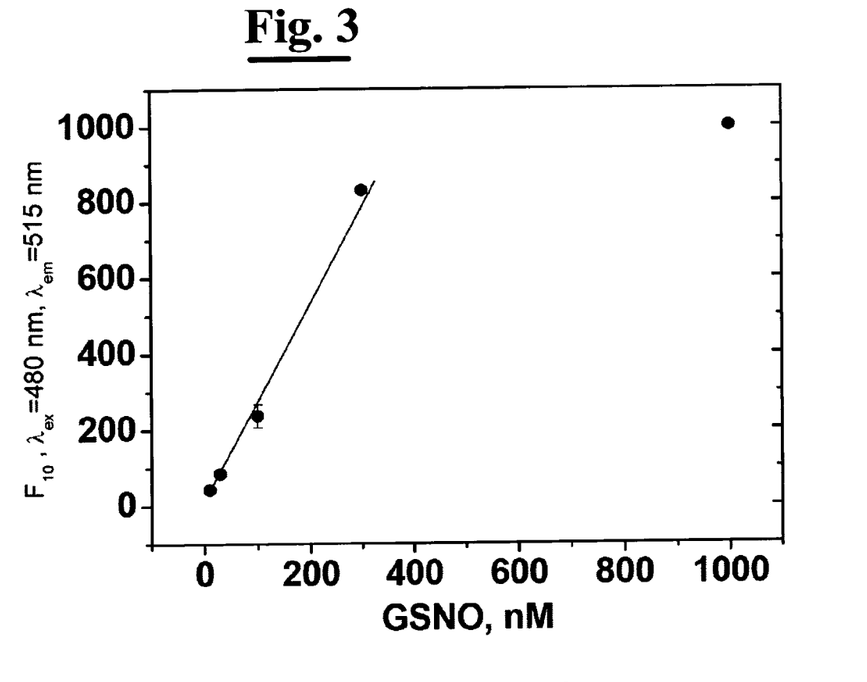
FIG. 3 shows a calibration curve of the standard solution of GSNO.

FIG. 3 shows the calibration curve of the standard solution of GSNO in PBS 0.1 M pH 8 determined by the reaction of GGT. The reaction mixture consists of: PBS 0,1 M pH 8, $CuSO_4$ 100 uM, in the 100 uM, GlyGly 4.5 mM, DAF 0,1 uM, GGT 525 mU/ml. GSNO (in the range 10-1000 nM) is added at the time t=0. In the ordinates the value of plateau is shown of the kinetic obtained after a time of 10 minutes ($F_{10}$ indicated in FIG. 2).

The method proposed in case of detection with DAF is linear in the range 10 nM-300 nM (parameters of the linear regression: slope=2.73±0.07; N=4; R=0.0079), has a revealability limit of 5 nM and a precision of 1% (CV %) at 300 nM of concentration level.

Control of the interfering molecules a) Interference due to transnitrosylation reactions. It is known that in real samples, such as plasma, GSNO can form artefactually owing to transnitrosylation reactions. Such reactions can be carried out between nitrosoalbumin and the reduced glutathione (GSH) present in the sample. This interference is controlled through the addition to the sample to analyse of an alkylating reagent of the thiolsc groups (—SH), N-ethylmaleimide (NEM). The NEM, by alkylating the free thiolsc groups inhibits the transnitrosylation reactions.

b) Since the reduced glutathione (GSH) is a substrate of GGT having higher affinity than GSNO (Km=5-10 µM), the GSH present in the samples can represent an interfering molecule for the analysis. Also this interference is controlled by the addition of NEM to the sample to analyse. Kinetics similar to that of FIG. 2 have been, therefore, carried out in the presence of GSH (up to 100 µM) and at 100 µM of NEM. The results show that the decomposition of GSNO by means of GGT is unchanged significantly with respect to those without GSH and NEM.

EXAMPLE 1

Computing Gsno In Mouse Heart Perfusate By Elisa Plates

A) Preparing the Standards for the Calibration Curve and the Reagents
a) Preparing 0.5 mL of standard solutions of GSNO (125, 375, 1250, 3750, 12500 nM) in phosphate buffer 0.1 M, pH 8.0, 0.5 mM EDTA (ethylenediaminetetraacetic acid);
b) Preparing 1 mL 112.5 mM GlyGly solution in 0.1 mM phosphate buffer and adjusting the pH to 8.0 with 0.1 M NaOH;
c) Preparing a 13.1 U/mL GGT solution (1 mL) in 0.1 M, pH 8.0 phosphate buffer;
d) Preparing a 2.5 MM Cu ($SO_4$) solution (5 mL) in bidistilled and deionized water;
e) Preparing a 5 mM NEM solution (5 mL) in bidistilled and deionized water;
f) Preparing a 2.5 uM DAF solution (1 mL) in 0.1 M, pH 8.0 phosphate buffer.

B) Preparing the Sample
a) For single determination triple 375 uL of isolated and perfused mouse heart perfusate are needed in a Langendorff system collected in 0.5 mM EDTA; for standard triple additions 1500 uL of perfusate are required.
b) Adding to the perfusate the mother solution in order to obtain a final concentration of 100 uM (for example: 30 uL in 1500 uL of perfusate).

C) Preparing the "White in the Well" Solution (Total Volume in the Well 250 ul)
a) 190 uL of 0.1 M, pH 8.0 phosphate buffer;
b) 20 uL of phosphate buffer 0.1 M, pH 8.0, 0.5 mM EDTA (replacing the analyte);
c) 10 uL GlyGly solution;
d) 10 uL DAF solution;
e) 10 uL GGT solution;
f) 10 uL $CuSO_4$ solution.

D) Preparing the Standard Solutions of Gsno in the Well (Total Volume in the Well 250 uL)
a) 190 uL of 0.1 M, pH 8.0 phosphate buffer;
b) 20 uL of GSNO standard solution (125, 375, 1250, 3750, 12500nM) in phosphate buffer 0.1 M, pH 8.0, 0.5 mM EDTA;
c) 10 uL GlyGly solution;
d) 10 uL DAF solution;
e) 10 uL GGT solution;
f) 10 uL $CUSO_4$ solution.

E) Preparing the Perfusate as Such in the Well (Total Volume in the Well 250 ul)
a) 65 uL of 0.1 M, pH 8.0 phosphate buffer;
b) 125 uL perfusate;
c) 20 uL of phosphate buffer 0.1 M, pH 8.0, 0.5 mM EDTA (replacing the spike of GSNO);
d) 10 uL GlyGly solution;
e) 10 uL DAF solution;
f) 10 uL GGT solution;
g) 10 uL $CuSO_4$ solution F) Preparing the Perfusate with Added Gsno Standard in the Well (Total Volume in the Well 250 ul)
a) 65 uL 0.1 M, pH 8.0 phosphate buffer;
b) 125 uL perfusate;

c) 20 uL GSNO standard solution (125, 375, 1250, 3750, 12500 nM) in phosphate buffer 0.1 M, pH 8.0, 0.5 mM EDTA;
d) 10 uL GlyGly solution;
e) 10 uL DAF solution;
f) 10 uL GGT solution;
g) 10 uL $CuSO_4$ solution G) Procedure of Analysis The solution of white, standard solutions and samples (as such and with added standard) are loaded in three ELISA wells to obtain a triple determination.

Figure 4:
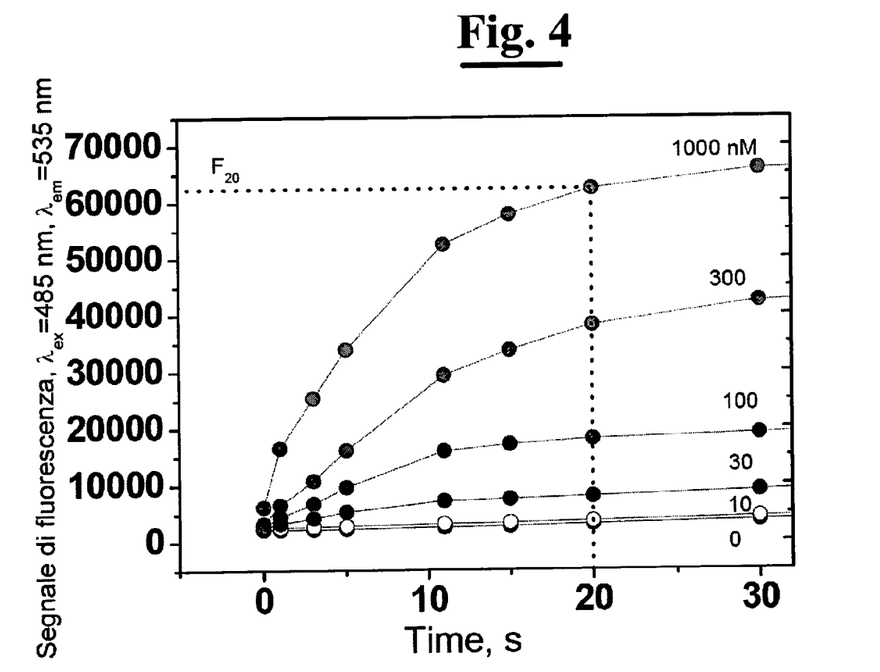
FIG. 4 shows the kinetic of formation of DAF-2T in a phosphate buffer at various concentrations of GSNO.

After preparing the last well the reading step of the fluorescence signal startsto at various time intervals. FIG. 4 shows the kinetic of formation of DAF-2T in the phosphate buffer at various concentrations of GSNO (10, 30, 100, 300, 1000 nM).

Figure 5:
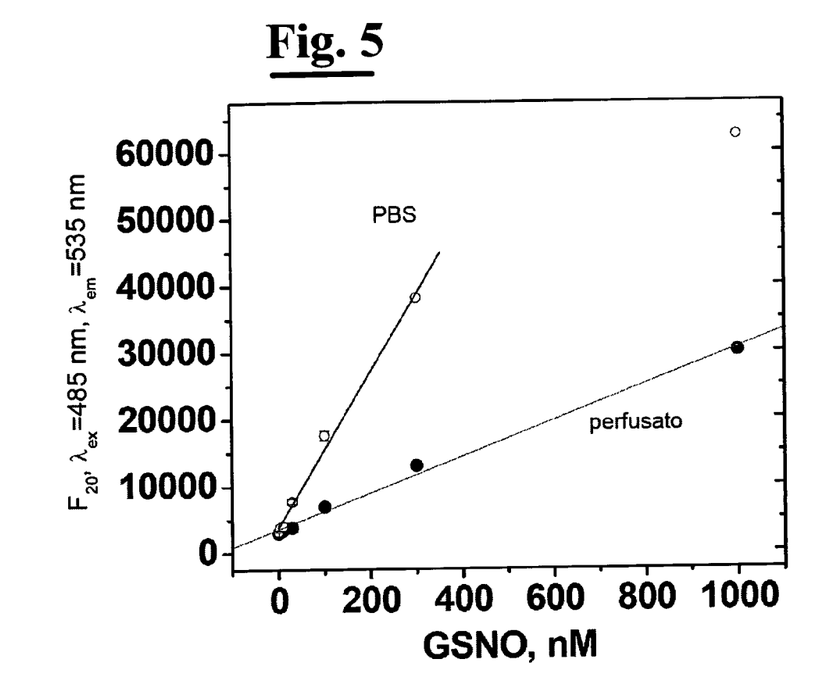
FIG. 5 shows a calibration curve of the standard solution of GSNO in PBS 0.1 M pH 8 and a curve of the standard additions to the perfusate.

FIG. 5 shows the calibration curve of the standard solution of GSNO in 0.1 M pH 8 PBS and the curve of the standard additions to the perfusate obtained from the proposed method. In ordinate the value is indicated of the plateau of the kinetics obtained after a time of 20 minutes ($F_{20}$ indicated in FIG. 4).

The slope of the line of linear regression in the perfusate (slope=26.9 ±1; R=0.9969; intercept=3552±453) is less than that obtained in the phosphate buffer (slope=117 ±5; R=0.9965; intercept=3756±636) owing to the matrix effect. This requires the use of the method of the standard additions for analysis of a complex matrix. It should be noted that the matrix effect is not observed where the analysis is carried out in a cuvette by means of spectrofluorimeter (see example 2) owing to a more accurate selection of the excitation and transmission wavelength.

From the results of the linear regression a limit of revealability is estimated in the system of reading in the plate of 30 nM in phosphate buffer.

In the considered perfusate sample the concentration of GSNO measured is 264±26 nM (considering the factor of dilution 1:1 of the perfusate in the well).

EXAMPLE 2

Computing Mouse Heart Perfusate Gsno By Spectrofluorimeter

A) Preparing the Standard for Calibration Curve and the Reagents a) Preparing 1 mL of standard solutions of GSNO (1, 3, 10, 30 and 100 uM) in phosphate buffer 0.1 M, pH 8.0, 0.5 mM EDTA (ethylendiaminetetraacetic acid );
b) Preparing 10 mL of solution of 200 mM GlyGly in 0.1 mM phosphate buffer and adjusting the pH to 8.0 with 0.1 M NaOH;
c) Preparing a solution of 12 U/mL GGT (5 mL) in phosphate buffer 0.1 M, pH 8.0;
d) Preparing a solution of 10 mM $Cu(SO_4)$ (5 mL) in bidistilled and deionized water;
e) Preparing a 10 mM NEM solution (5 mL) in bidistilled and deionized water;
f) Preparing a 10 uM DAF solution (1 mL) in 0.1 M, pH 8.0 phosphate buffer;

B) Preparing the Sample a) For each determination 500 uL of isolated and perfused mouse heart perfusate are needed in Langendorff system collected in 0.5 mM EDTA.
b) Adding to the perfusate the mother solution in order to obtain a final concentration of 100 uM (5 uL in 500 uL of perfusate).

C) Spectrofluorimetric Analysis in 1 mL Cuvette

The reaction mixture consists of:
a) 404 uL of 0.1 M, pH 8.0 phosphate buffer;
b) 500 uL of perfusate (or 500 uL of phosphate buffer 0.1 M, pH 8.0, 0.5 mM EDTA, 100 uM NEM if the calibration curve of GSNO is carried out in the buffer);
c) 10 uL of solution of $CuSO_4$.
d) 22.5 uL GlyGly solution;
e) 43.7 uL GGT solution;
f) 10 uL DAF solution;
g) 10 uL of phosphate buffer 0.1 M, pH 8.0, 0.5 mM EDTA in the case where a white has to be carried out or the analysis as such of the perfusate or 10 uL of standard solutions of GSNO at various concentrations for tracing the calibration curve or the standard additions curve. After the latter addition the acquisition of the fluorescence signal is started at various time intervals.

Figure 6:
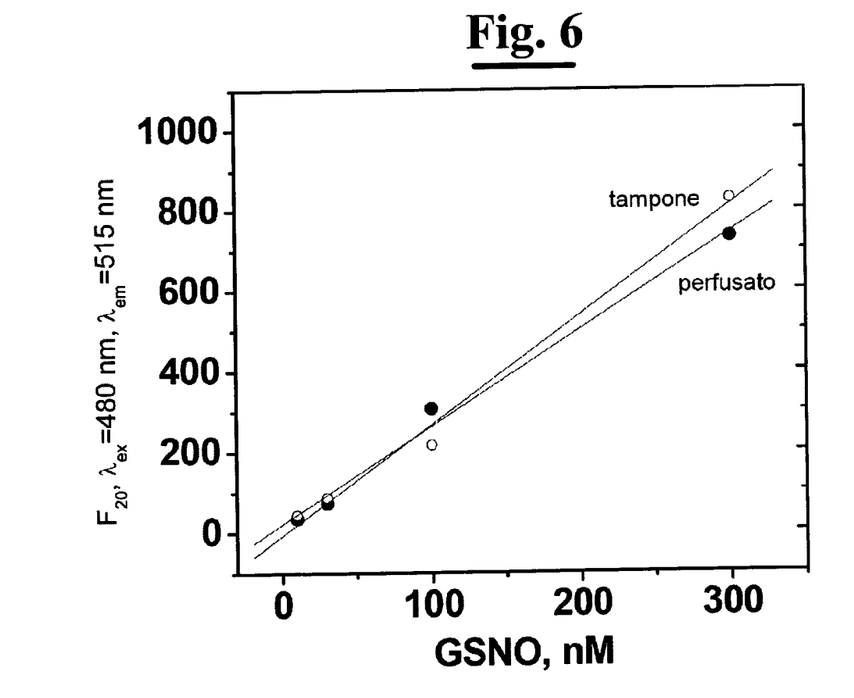
FIG. 6 shows a calibration curve of GSNO in a buffer and the curve of the standard additions in the perfusate.

FIG. 6 shows the calibration curve of GSNO in a buffer (O) (slope=2.7±0.11; R=0.9957; intercept=0) and the curve of the standard additions in perfusate (●) (slope=2.41±0.16; R=0.9958; intercept=20.6±25). In the perfusate the concentration of GSNO is less than the limit of strumental detection (30 nM in the perfusate).

Figure 7:
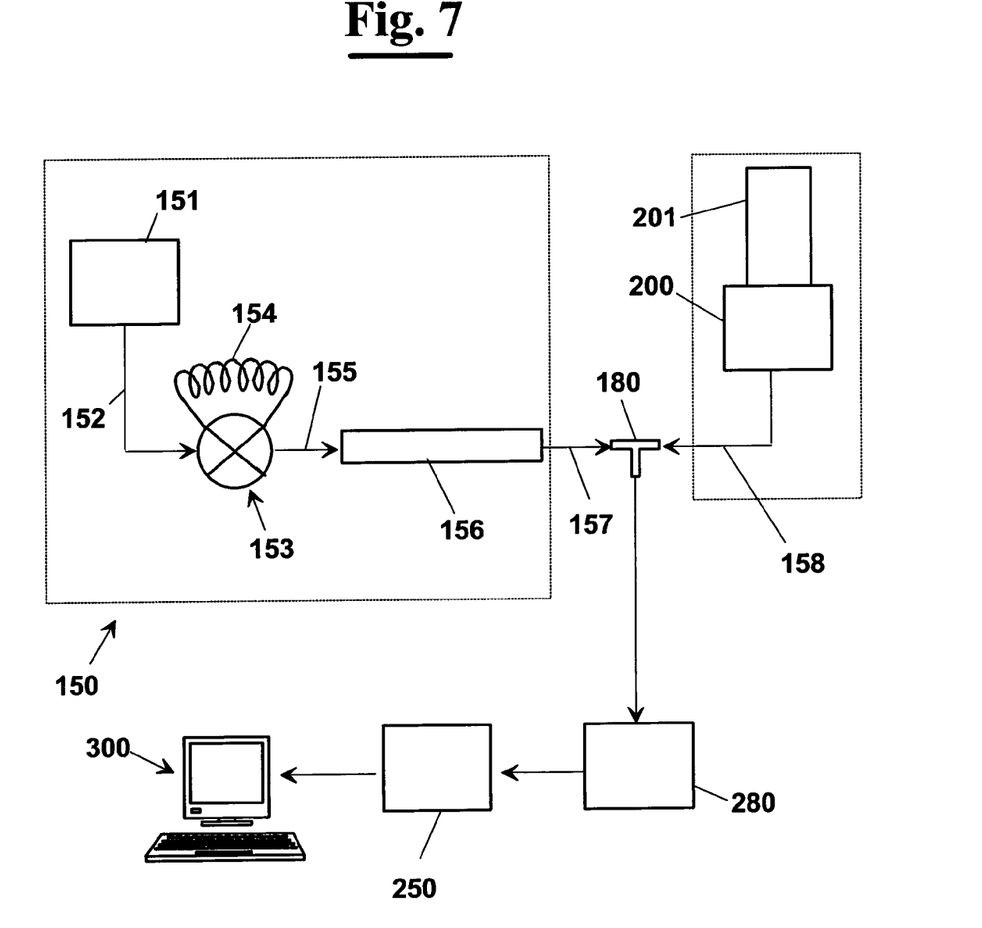
FIG. 7 shows diagrammatically an apparatus for determining the content of S-nitrosothiols in biological fluids, in particular, in case of biological fluids having complex matrix.

In FIG. 7 an apparatus 100 is diagrammatically shown for determining the content of S-nitrosothiols in biological fluids, in particular, in case of biological fluid having complex matrix, for example plasma. Apparatus 100 comprises a device 150 for high pressure liquid chromatography (HPLC) equipped with a pump 151 connected through a duct 152 to an injection valve 153. Injection valve 153 has a loop 154 through which the sample to analyse is inserted and is connected through a duct 155 to a separative column 156. In separative column 156 the separation is carried out of the different components of plasma that exit from the column 156 through a duct 157 at different times. Then, the only components touch a derivatization mixture at a fitting 180.

In particular, the derivatization mixture reaches fitting 180 through a duct 158 pushed by a pump 200 for example a perfusor for clinical use. In particular, the pump 200 draws the derivatization mixture from a reservoir 201 in which it had been previously put into. The derivatizing mixture comprises, for example, a phosphate buffer 0.5 M (pH: 8.0), GGT: 525 mU/ml adapted to react with GSNO causing the catalytic decomposition, copper sulphate: 100 μM, glycidine (GG): 4.5 mM and DAF: 1.2 μM. The latter converts the not fluorescent molecule into a molecule capable of emitting luminous waves by means of chemical reaction allowing the detection by a detector 250 arranged downstream of T fitting 180.

The derivatizing mixture, containing the GGT enzyme, is then mixed in continuous flow with the eluate coming from the chromatographic column 156, thus reacting, or not reacting, only with the nominally pure components that exit from the chromatographic column. More in detail, the enzymatic reaction is specific and selective for GSNO whereby the fluorescence signal derived from the reaction of freed NO in solution with DAF is observed only at the exit from GSNO column. The amount of GSNO is then calculated, for example by a PC 300 that determines and/or checks the substances injected through the amount of released nitric oxide. The detector can be for example a spectrophotometric detector, or a fluorimetric detector, or an electrochemical detector.

Before reaching detector 250, the derivatizing mixture and GSNO can be sent to a thermostatic bath 280 for increasing the speed of the enzymatic decomposition reaction.

Figure 8A:
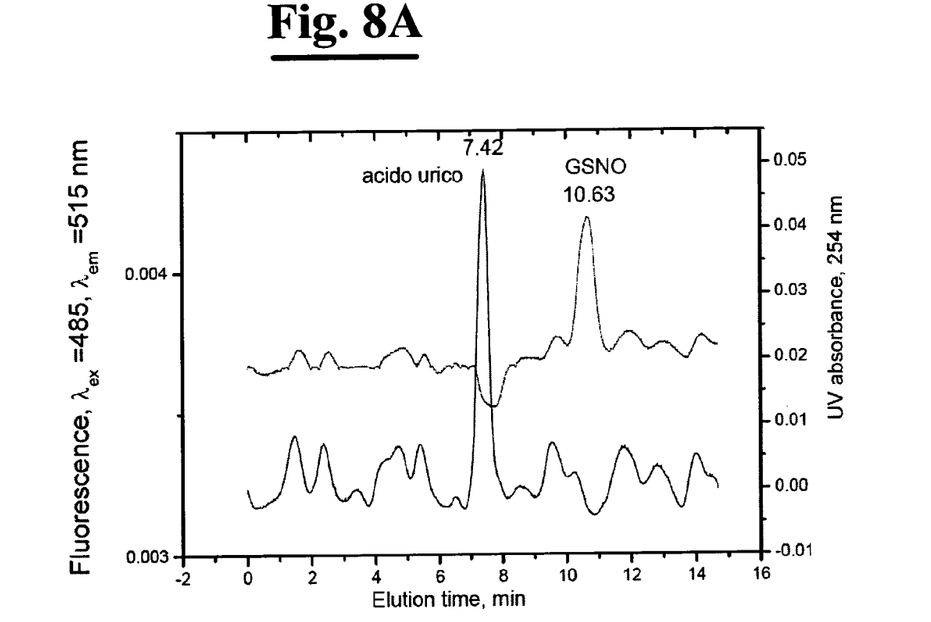
FIG. 8A shows the typical chromatogram of a mixture of commercial commercial standards of GSNO 100 nM and uric acid 50 uM in 0.1 M PBS pH 8.0 used in the apparatus of FIG. 7.
Figure 8B:
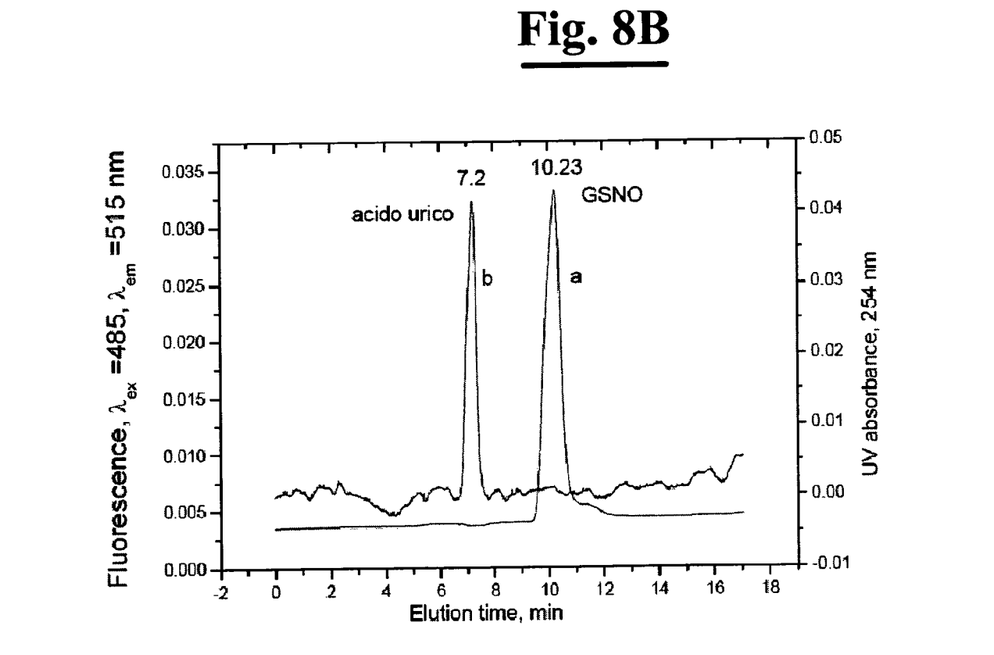
FIG. 8B shows the typical chromatogram of a mixture of commercial standards of GSNO 1000 nM and uric acid 50 uM in 0.1 M PBS pH 8.0 used in the apparatus of FIG. 7, where (a) is a fluorescence chromatogram ($\lambda ex=485$ nm and $\lambda em=515$ nm) and with (b) an UV chromatogram at $\lambda=254$ nm.

FIGS. 8A and 8B show a typical chromatogram of a mixture of commercial standards of 100 nM (A) and 1000 nM (B)

GSNO and 50 uM uric acid in 0.1 M pH 8.0 PBS injected in the apparatus of FIG. 7. In particular, uric acid has been chosen as example of antioxidant molecule present in plasma at high concentration (257±71) (65). Line (a) indicates the UV chromatogram recorded at 254 nM that shows the eluition of uric acid at a tR of 7.2 min. Line (b) indicates the fluorescence chromatogram that shows the peak value of GSNO at tR=10.23 min. In this specific case two detectors in series (UV and fluorimetric) have been used for tracing the eluition of the two components. It is noticeable that uric acid is separated from the chromatographic column and does not interfere with the detection of GSNO and that the enzymatic reaction of derivatization is selective for GSNO.

Figure 9:
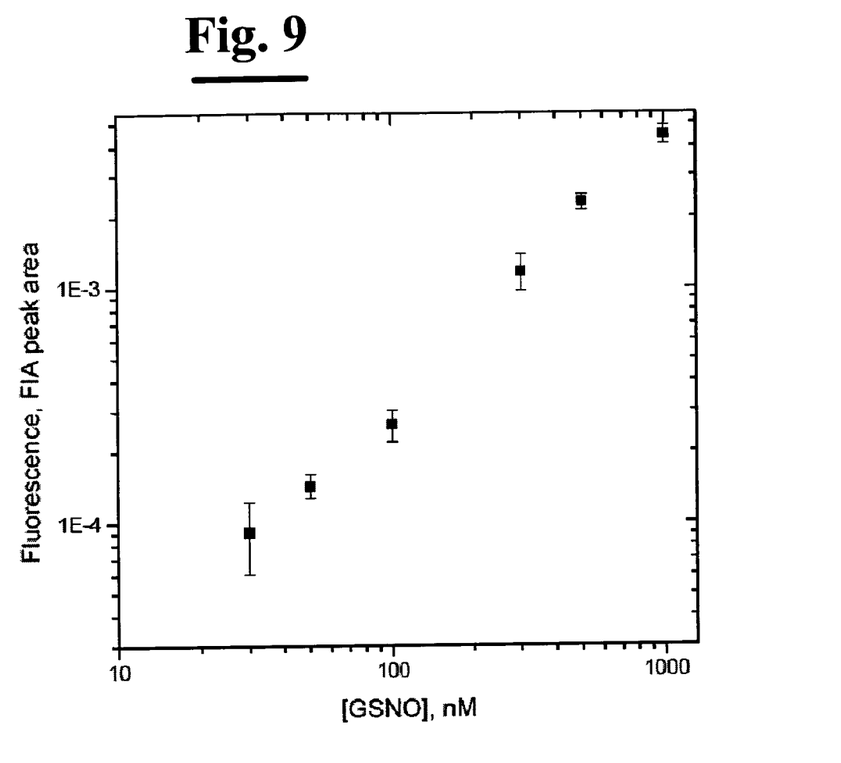
FIG. 9 shows the calibration curve of GSNO obtained injecting different concentrations of GSNO in the apparatus of FIG. 7.

FIG. 9 shows the calibration curve of GSNO obtained injecting GSNO at different concentrations in the apparatus of FIG. 7, in the operative conditions given in table 1 located underneath in which are indicated the optimal conditions for determining GSNO by means of liquid chromatography coupled to on-line post-column derivatization with DAF and spectrofluorimetric detection ($\lambda$ex=485 nm and $\lambda$em=515 nm).

TABLE 1

| | |
|---|---|
| HPLC flow | 1 mL/min |
| Derivatizing mixture flow | 0.5 mL/min |
| Volume of injected sample ($V_{inj}$) | 100 microL |
| Volume of the reaction coil | 2.6 mL |
| Temperature of the thermostatic bath | 37° C. |

The points are linear in the range of two orders of magnitude (10 nM-1000 nM is the studied range), with a factor of sensitivity of 4.42±0.11 10-6 unity/nM (R=0.9988, N=6points) and a detection limit of 10 nM (detection limit, LODc=3nM).

In particular, the calibration curve of FIG. 9 has been made with FIA technique (Flow Injection Analysis), i.e. with the apparatus of FIG. 7, but without chromatographic column. This technique determines a similar response (area of the peak) to that obtained in the presence of the separative column, but in a shorter time (4 minutes against 15 minutes) and can be advantageously used when the sample injected is a standard commercial for calibration of the system or all the times where the sample to analyse does not contain interfering molecules (anti-oxidant, anti-free radicals molecules).

EXAMPLE 3

Computing Gsno in Human Plasma
A) Preparing the Standard for Calibration Curve and the Reagents
a) Preparing 0.5 mL of standard solutions of GSNO (10, 30, 50, 100, 300, 500 1000nM) in phosphate buffer 0.1 M, pH 8.0;
b) Preparing 10 mL of 200 mM GlyGly solution in phosphate buffer 0.1 M and adjusting the pH to 8.0 with 0.1 M NaOH;
c) Preparing a solution of 100 U/mL GGT (10 mL) in 0.1 M, pH 8.0 phosphate buffer;
d) Preparing a solution of 10 mM Cu(SO$_4$) (5 mL) in bidistilled and deionized water;
e) Preparing a 100 mM NEM solution (5 mL) in bidistilled and deionized water;
f) Preparing a 500 uM DAF solution (5 mL) in phosphate buffer 0.1 M, pH 8.0.
B) Preparing the Chromatographic Eluent Phase and Description of the Chromatographic Separation Conditions
a) Chromatographic column: reverse phase column (RPC) of type C18 with particles of 5 um diameter, length 25 cm, diameter 4.6 mm (for example Gemini Phenomenex column);
b) Eluent: 20 mM phosphate buffer, pH 6.0 containing 3% of methanol;
c) Loop=100 uL (injection volume);
d) Conditions of isocratic eluition with 1 mL/min flow.
C) Preparing the Reaction Mixture of Post-Column Derivatization
50 mL are prepared of 0.5 M phosphate buffer, pH 8.0 containing:
a) γ-glutamyltranspeptidase (GGT)525 mU/mL;
b) 100 microM Copper sulphate;
c) 4.5 mM Glycylglycine (GG);
d) 1.2 microM. DAF
D) Preparing the Sample
The whole peripheral blood (5 mL) is sampled in the presence of 0.5 mM EDTA (ethylendiaminetetraacetic acid as anticoagulating and in the presence of 12 mM of NEM (N-ethyl maleimide), an alkylating agent of the free thiolsc groups (—SH). The use of NEM is necessary for controlling the transnitrosylation reactions. In fact, it is known that in real samples such as plasma, GSNO can form artefactually, owing to transnitrosylation reactions. Such reactions can be carried out between nitrosoalbumin and the reduced glutathione (GSH) present in the sample. NEM, by alkylating the free thiolsc groups, inhibits the transnitrosylation reactions.

The blood is then centrifugated at 1000×g for 10 minutes at 4° C. for removing the corpuscolated parts and to obtain plasma.

The plasma thus obtained has to be deproteinized. This step can be carried out according to two alternative procedures, i.e. the acid precipitation, or ultracentrifugation, described hereafter.

Acid Precipitation
Addition to 500 uL plasma of 10 uL of 50% sulphosalicylic acid (SSA) (TCA) followed by centrifugation at 1000×g for 5 min at 4° C. The supernatant is injected triple in the system described with reference to FIG. 7.

Figure 10A:
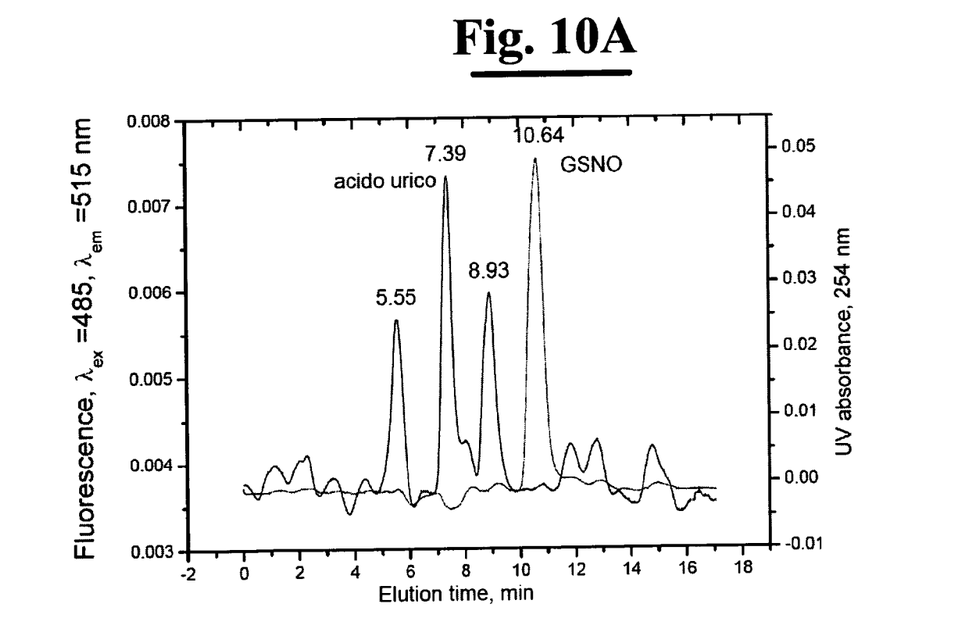
FIGS. 10A and 10B show the UV and fluorescence chromatograms of a sample of deproteinized plasma by means of ultrafiltering for different concentrations of GSNO, respectively 100 nM (FIG. 10A) and 500 nM (FIG. 10B)
Figure 10B:
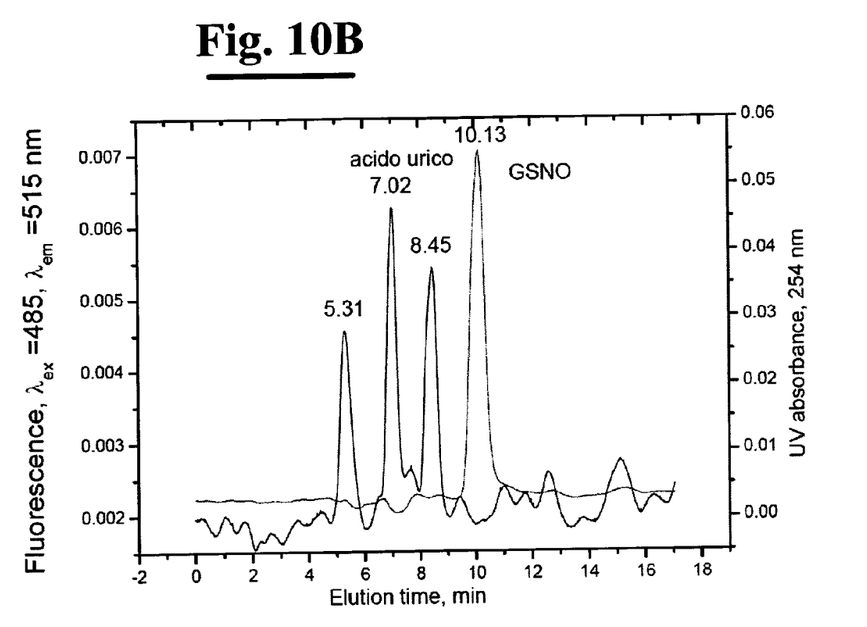

Ultracentrifugation of Plasma
The ultracentrifugation of plasma is made with membrane filters Amicon Microcon YM-3 cut-off 3,000 (commercial: Millipore, Bedford, Mass., USA) at 7000×g for 2 h at 4° C. The ultrafiltered matter is injected triple in the system described with reference to FIG. 7.
E) Procedure of Analysis
The apparatus is calibrated by injecting solutions of standard commercial GSNO in 0.5 M pH 8.0 phosphate buffer in the concentration range 10-1000 nM. The area of the peak value of GSNO at tR=10.23 min is shown in the chart versus the injected concentration obtaining the calibration curve.
F) Analysis of Deproteinized Plasma
In loop 154 of FIG. 7 a sample of deproteinized plasma is injected. In FIG. 10 an example is given of the UV and fluorescence chromatogram of a sample of plasma with standard addition of 100 nM (figure A) and 500 nM (figure B) GSNO. GSNO concentration is measured on the basis of the area of the peak value at tR=10.13 and on the basis of the calibration curve. In the example the recovered GSNO added to plasma has been 97±5%.

Figure 11:
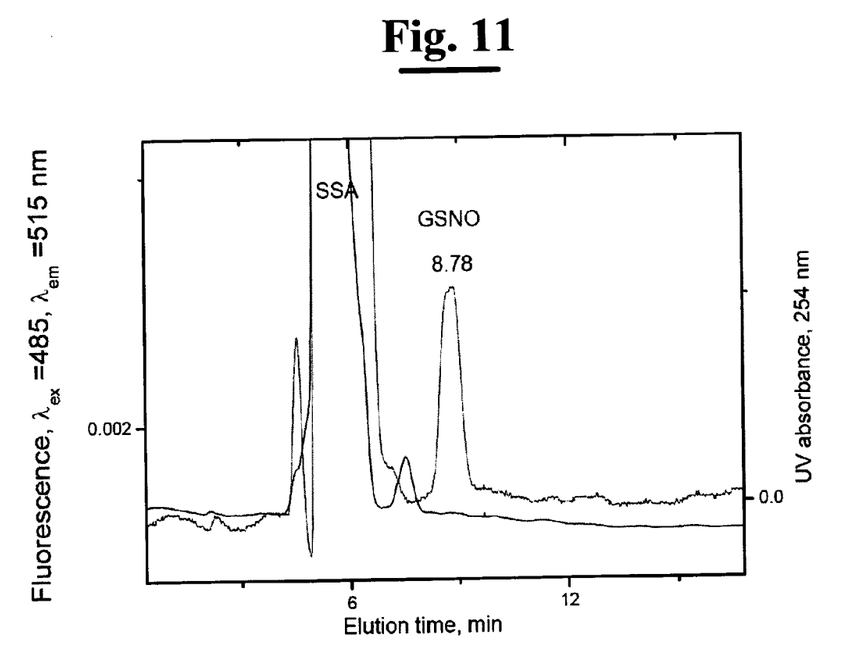
FIG. 11 shows the UV and fluorescence chromatogram of a sample of plasma with standard addition of GSNO 100 nM deproteinized with acid precipitation in SSA 1%.

In FIG. 11 an example is given of the UV and fluorescence chromatogram of a sample of plasma with standard addition of 100 nM GSNO deproteinized with acid precipitation in SSA 1%. The out-of-scale peak value in the fluorescence chart is fluorescent sulphosalicylic acid, which however elutes first from the column and does not interfere with the detection of GSNO (peak at tR=8.78 min). This procedure of deproteinization has the advantage of requiring 5 min instead of 2 hours necessary for ultrafiltering.

The invention claimed is:

1. Process for determining the concentration of S-nitrosothiols in biological fluids which comprises the following steps:
    adding a biological fluid sample in a container,
    introducing in said container a measured amount of the enzyme γ-glutamyl -transpeptidase (GGT), causing a catalytic decomposition of S-nitrosothiols into an intermediate nitrosylated product with subsequent release of nitric oxide (NO), or a derivative thereof, and
    determining the amount of released nitric oxide, or of a derivative thereof, said amount being proportional to the S-nitrosothiol amount present in said sample,
    correlating the amount which is proportioned to the S-nitrosothiols.

2. Process for determining S-nitrosothiols in biological fluids, according to claim 1, wherein said S-nitrosothiol is S-nitrosoglutathione.

3. Process for determining of the concentration of S-nitrosothiols in biological fluids, according to claim 1, wherein said amount of nitric oxide present in said sample is measured through a reaction thereof with a fluorescent molecule, said reaction creating a fluorescent compound in an amount proportional to the S-nitrosothiol amount present in the sample.

4. Process for determining the concentration of S-nitrosothiols in biological fluids, according to claim 3, wherein said fluorescent molecule is 4,5 diaminofluorescein (DAF-2).

5. Process for determining the concentration of S-nitrosothiols in biological fluids, according to claim 1, wherein said amount of released NO is measured by a chemiluminescence analyser.

6. Process for determining the concentration of S-nitrosothiols in biological fluids, according to claim 1, wherein said derivative of released nitric oxide is selected from the group consisting of
    dinitrogen trioxide $N_2O_3$ and
    ione nitrite NO.

7. Process for determining the concentration of S-nitrosothiols in biological fluids, according to claim 1, wherein said catalytic decomposition is carried out using as catalyst a transition metal.

8. Process for determining the concentration of S-nitrosothiols in biological fluids, according to claim 1, wherein said introduction in said container of said measured amount of said enzyme is done downstream of a flow-injection apparatus (FIA).

9. Process for determining the concentration of S-nitrosothiois in biological fluids, according to claim 3, wherein said introduction in said container of said measured amount of said enzyme is made after separating said S-nitrosothiol.

10. Process for determining the concentration of S-nitrosothiols in biological fluids, according to claim 9, wherein said step of separating said S-nitrosothiol from said other components of said organic fluid is effected by a separative technique in liquid phase selected from the group consisting of:
    liquid chromatography, high pressure liquid chromatography (HPLC)capillary electrophoresis; and precipitation in liquid phase.

11. Process for determining the concentration of S-nitrosothiols in biological fluids, according to claim 10, wherein said enzyme is mixed in continuous flow with an eluate coming from a chromatographic column in which the separation is carried out of said biological fluid into its components, said enzyme contacting separately the components of said eluate and reacting only with the S-nitrosothiol causing said catalytic decomposition.

12. Process for determining the concentration of S-nitrosothiols in biological fluids, according to claim 11, wherein said enzyme is mixed in a continuous flow with said eluate after mixing it with a measured amount of a fluorescent molecules obtaining a derivatizing mixture, said fluorescent molecules reacting with an intermediate nitrosylated product creating a fluorescent compound in an amount proportional to the amount of said S-nitrosothiol present in the biological fluid sample.

13. Process for determining the concentration of S-nitrosothiols in biological fluids, according to claim 11, wherein said derivatizing mixture is supplied to a thermostatic bath adapted to increase the speed of said enzymatic decomposition reaction.

14. Process for determining S-nitrosothiols in biological fluids, according to claim 10, by high pressure liquid chromatography (HPLC).

* * * * *